US00PP35774P2

(12) United States Plant Patent
Olesen

(10) Patent No.: US PP35,774 P2
(45) Date of Patent: Apr. 30, 2024

(54) ROSE PLANT NAMED 'POULPAH113'

(50) Latin Name: *Rosa hybrida*
Varietal Denomination: Poulpah113

(71) Applicant: Mogens Nyegaard Olesen, Fredensborg (DK)

(72) Inventor: Mogens Nyegaard Olesen, Fredensborg (DK)

(73) Assignee: Poulsen Roser A/S, Fredensborg (DK)

( * ) Notice: Subject to any disclaimer, the term of this patent is extended or adjusted under 35 U.S.C. 154(b) by 0 days.

(21) Appl. No.: 18/445,496

(22) Filed: Sep. 8, 2023

(30) Foreign Application Priority Data

Sep. 30, 2022 (QZ) ..... PBR 2022/2162

(51) Int. Cl.
*A01H 5/02* (2018.01)
*A01H 6/74* (2018.01)

(52) U.S. Cl.
USPC ..... Plt./116
CPC ..... *A01H 6/749* (2018.05)

(58) Field of Classification Search
USPC ..... Plt./116
CPC ..... A01H 6/749; A01H 5/02
See application file for complete search history.

*Primary Examiner* — Keith O. Robinson

(57) ABSTRACT

A new garden rose plant of the Miniature class which has abundant, pink and white striped flowers and attractive foliage. This new and distinct variety has shown to be uniform and stable in the resulting generations from asexual propagation.

2 Drawing Sheets

Botanical : *Rosa hybrida.*

Variety denomination: 'Poulpah113'.

This application claims priority to Plant Breeder's Rights Application Number 2022/2162, which was filed at the Community Plant Variety Rights Office in the European Union on Sep. 26, 2022, the contents of which are hereby incorporated by reference for all purposes.

SUMMARY OF THE INVENTION

The present invention constitutes a new and distinct variety of rose plant which originated from a controlled crossing between the female seed parent, an unnamed seedling, and the male pollen parent, also an unnamed seedling. Both of the parent varieties are non-patented.

The two parents were crossed during the summer of 2015 and the resulting seeds were planted in a controlled environment in Fredensborg, Denmark. The new variety, named 'Poulpah113', originated as a single seedling from the stated cross.

The new variety may be distinguished from its male pollen parent and female seed parent primarily by the following characteristics. The male pollen parent plant has pink flowers while the new variety has pink and white striped flowers. The female seed parent plant has deep pink flowers while the new variety has pink and white striped flowers.

The objective of the hybridization of this rose variety was to create a new and distinct variety with unique qualities, such as:

1. Uniform and abundant pink and white striped flowers;
2. Vigorous, but compact growth when propagated on its own roots;
3. Exceptional disease resistance.

This combination of qualities is not present in previously available commercial cultivars of this type, known to the inventor, and distinguish 'Poulpah113' from all other varieties of which we are aware.

As part of the rose development program, Mogens N. Olesen germinated the seeds from the aforementioned hybridization during winter of 2015 and conducted evaluations on the resulting seedlings in a controlled environment in Fredensborg, Denmark. 'Poulpah113' was selected in the spring of 2016 by the inventor as a single plant from the progeny of the aforementioned hybridization.

Asexual reproduction of 'Poulpah113' by rooted cuttings was first done by Mogens N. Olesen in the nursery in Fredensborg, Denmark in July, 2016. This initial and other subsequent asexual propagations conducted in controlled environments have demonstrated that the characteristics of 'Poulpah113' are true to type and are transmitted from one generation to the next.

DESCRIPTION OF THE DRAWING

The accompanying color illustrations show as true as is reasonably possible to obtain in color photographs of this type, the typical characteristics of the buds, flowers, leaves, and stems, of 'Poulpah113'.

Specifically illustrated in FIG. 1 of the drawings are open flowers viewed from the side and above, flower buds at various stages of opening, petals detached, and sepals detached revealing reproductive flower parts, and receptacle.

Figure 1:
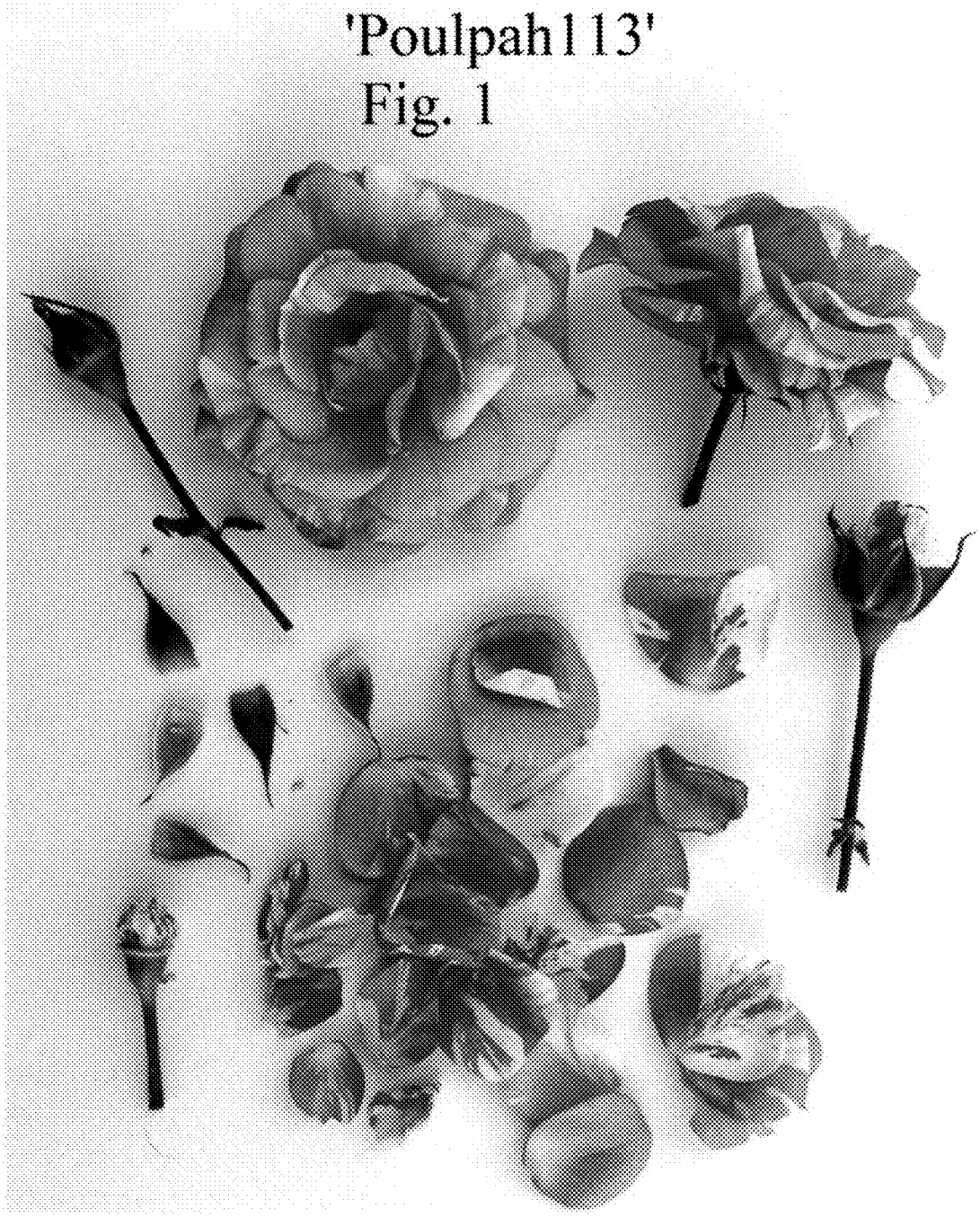
Figure 2:
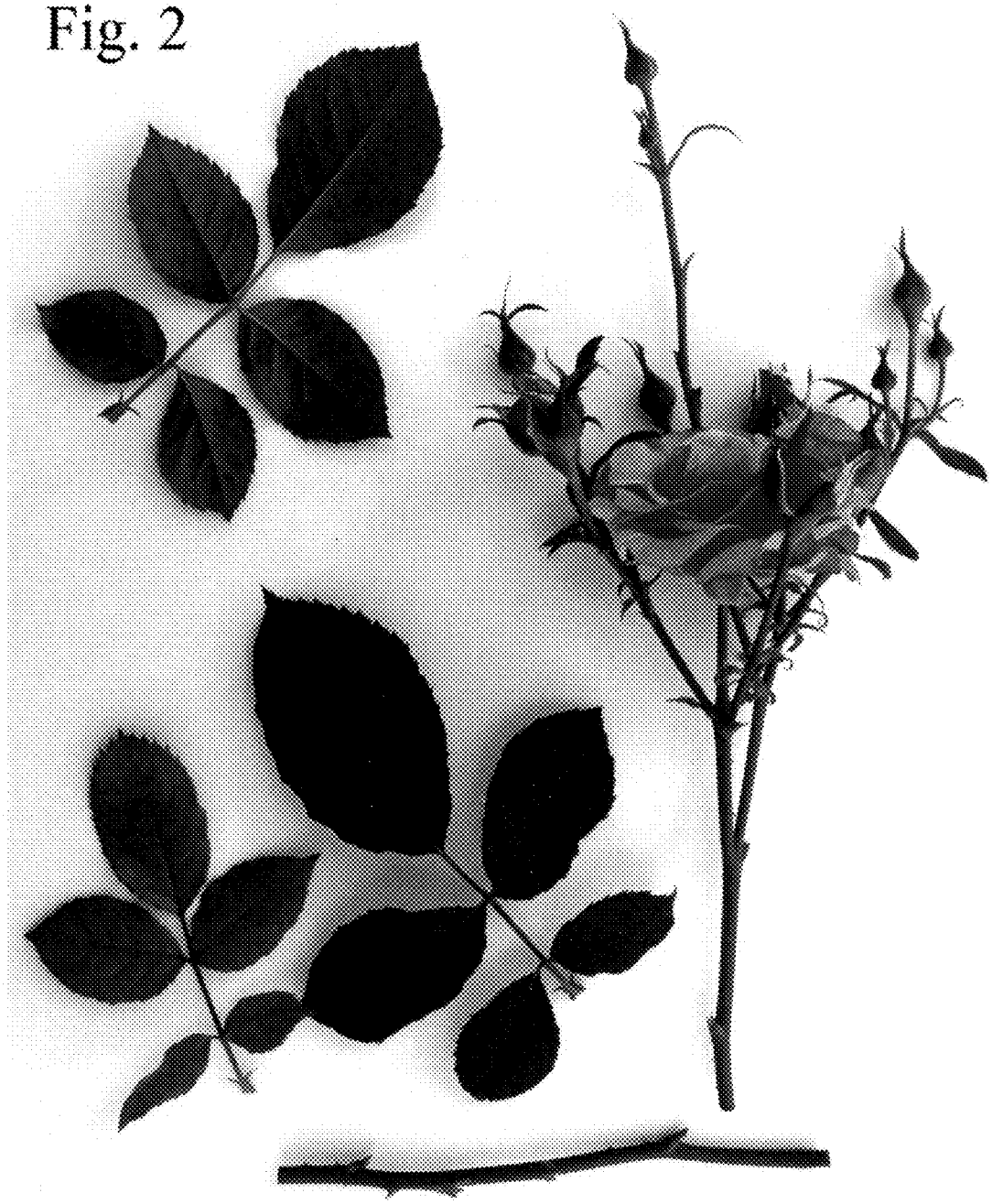

Specifically illustrated in FIG. 2 of the drawings are a cluster of flowers and flower buds on a branch, bare stem exhibiting prickles, and mature and juvenile leaves. Plants shown are 5 months years of age.

DETAILED DESCRIPTION OF THE VARIETY

The following is a description of 'Poulpah113', as observed in its growth in an indoor nursery in Odense Denmark. Observed plants are 5 months of age, and were grown on their own roots in 19 cm pots. Color references are made using The Royal Horticultural Society (London, England) Colour Chart, 2001, except where common terms of color are used.

For a comparison, several physical characteristics of the rose variety 'Poulpah086', U.S. Plant Pat. No. 29,701 are compared to the claimed plant. The upper surface of outer petals of 'Poulpah113' are Red-Purple Group 65A with stripe intonations of White Group 155B, while the comparison variety 'Poulpah086' is Red Group 55C with intonations of Red Group 36A toward basal zone. The claimed plant has a flower diameter of 80 mm while 'Poulpah086' has a flower diameter of 55 mm.

FLOWER AND FLOWER BUD

Blooming habit: Continuous.

Flower bud:

- *Size.*—Upon opening, 24 mm in length from base of receptacle to end of bud. Bud diameter is 14 mm.
- *Bud form.*—Globose.
- *Bud color.*—As sepals divide petals are Red-Purple Group N57A, White Group 155C.
- *Sepal inner surface.*—Color: Yellow-Green Group 146D. Surface: Lightly pubescent.
- *Sepal outer surface.*—Color: Yellow-Green Group 144A. Texture: Rough with stipitate glands.
- *Sepal shape.*—Apex: Cirrhose. Base: Flat at union with receptacle.
- *Sepal margin.*—Margins have light or no foliaceous appendages on three of the five sepals.
- *Sepal size.*—25 mm long, 11 mm wide.
- *Receptacle.*—Texture: Smooth. Size: 8 mm in height, 10 mm wide. Color: Yellow-Green Group 144A. Shape: Funnel.
- *Pedicel.*—Surface: Rough with stipitate glands. Length: 38 mm. Diameter: 2 mm on average. Color: Yellow-Green Group 144A. Strength: Strong.
- *Peduncle.*—Length: 5 cm. Diameter: About 3 mm. Color: Yellow-Green Group 145A. Texture: Somewhat rough with small prickles Prickles Yellow-Green Group 145C.

Flower bud development: Flower buds are borne in clusters of 3 to 5 flower buds per stem.

Flower bloom:

- *Fragrance.*—Moderate, lemon fragrance.
- *Duration.*—The blooms have a duration on the plant of approximately 21 days. Petals fall cleanly away from plant after flowers have fully matured.
- *Size.*—Flower diameter is about 85 mm when open. Flower depth is 35 mm.
- *Flower shape.*—Open cup with petals that curve out from the center.
- *Shape of flower, side view.*—The upper portion is convex. The lower portion is concave.

Petalage: Under normal conditions, flowers have about 40 petals.

General tonality of flower: Open flowers are Red-Purple Group N57D, Red-Purple Group 65A, White Group N155B.

Petal color:

- *Upon opening, outer petals.*—Upper surface: Red-Purple Group 65A with stripe intonations of White Group 155B. A small area of coloration of Yellow Group 4B at the basal zone. Lower surface: Red-Purple Group N66C with stripe intonations White N155B.
- *Upon opening, inner petals.*—Upper surface: Red-Purple Group 62A with stripe of Yellow Group 4D. Lower surface: Red-Purple Group N57C with stripe intonations of Yellow Group 4D.
- *After opening, outer and inner petals.*—Upper surface: Red Group 68B with stripe White 155B. Lower surface: Red-Purple Group 68A with stripe White Group 155B.
- *Basal petal spots.*—After opening no distinctive coloration at the petal base observed.

Petals:

- *Petal reflex.*—Somewhat reflexed.
- *Margin.*—Entire and uniform. Moderate undulations.
- *Shape.*—Broad and elliptic. Apex shape: Rounded. Base shape: Acute.
- *Size.*—40 mm (l)×50 mm (w).
- *Texture.*—Smooth.
- *Thickness.*—Average.

Petaloids:

- *Size.*—12 mm (l) by 9 mm (w).
- *Quantity.*—About 3.
- *Shape.*—Elliptical with an acute base and acute apex.
- *Color.*—Red-Purple Group 62A with stripe of Yellow Group 4D on the upper and lower side.

Reproductive flower parts:

- *Pollen.*—None observed.
- *Anthers.*—Size: 2 mm in length. Color: Yellow Group 2D. Quantity: 36 on average.
- *Filaments.*—Color: Yellow Group 13A. Length: 5 mm.
- *Pistils.*—Length: 10 mm. Quantity: 26 on average.
- *Stigmas.*—Color: White Group 155A.
- *Styles.*—Color: White Group 155A.
- *Location of stigmas.*—Level in location relative to the length of the filaments and the height of the anthers.
- *Hips.*—None Observed.

PLANT

Plant growth: Upright. Plants are about 45 cm in height, and 35 cm wide.

Stems:

- *Color of juvenile growth.*—Yellow-Green Group 144B.
- *Color of mature growth.*—Yellow-Green Group 144A.
- *Length.*—Canes are about 15 cm from the base of the plant to the flowering portion.
- *Diameter.*—About 5 mm.
- *Internodes.*—On mature canes about 40 mm between nodes.
- *Surface texture.*—Young wood: Smooth. Older wood: Rough with small prickles.

Long prickles:

- *Incidence.*—3 prickles per 10 cm of stem.
- *Size.*—Average length of prickles on mature stems is 3 mm.
- *Shape.*—Upper portion is linear. Lower portion is concave.
- *Color.*—Juvenile prickles: Greyed-Orange Group N170D. Mature prickles: Greyed-Orange Group N170D.

Plant foliage:

- *Compound leaf.*—150 mm (l) by 115 mm (w).
- *Quantity.*—2 leaves per 10 cm of stem on average.

*Leaf bearing angle to the stem.*—45 degrees.

*Color of juvenile foliage*.—Upper side: Yellow-Green Group 144A with intonations of Greyed-Orange Group 175A on rachis. Lower side: Yellow-Green Group 144B.

*Color of mature foliage*.—Upper side: Yellow-Green Group 147A. Lower side: Yellow-Green Group 147B.

Plant leaves and leaflets:

*Stipules*.—Size: 11 mm long, 3 mm wide. Quantity: 2 per compound leaf. Shape: Linear, slightly broad based with outward extending apices. Margins: Finely serrated. Color: Yellow-Green Group 147A.

*Petiole*.—Length: 16 mm. Diameter: 2 mm. Upper surface color: Yellow-Green Group 144A. Lower surface color: Yellow-Green Group 144A.

*Rachis*.—Length: About 45 mm. Upper surface color: Yellow-Green Group 144A. Lower surface color: Yellow-Green Group 144A.

*Leaflet*.—Quantity: Normally 5 leaflets. Margins: Serrated. Size: Terminal leaflets are about 90 mm long, 50 mm wide. Shape: Generally elliptical. Base: Rounded. Apex: Mucronate. Texture: Smooth. Thickness: Average. Arrangement: Odd pinnate. Venation: Reticulate. Glossiness: Glossy.

Disease resistance: Above average resistance to powdery mildew *Sphaerotheca pannosa* var. *rosae*, downy mildew *Peronospora sparsa*, rust *Phragmidium* spp., black spot *Diplocarpon rosae*, and *Botrytis cinerea* under normal growing conditions.

Cold hardiness: The variety is tolerant to USDA Cold Hardiness Zone 6.

Heat tolerance: The variety has been found to be suitable for climate conditions found in the American Horticulture Society heat zone 7.

I claim:

1. A new and distinct variety of rose plant named 'Poulpah113' substantially as described and illustrated herein.

* * * * *

'Poulpah113'

'Poulpah113'